US012632111B2

(12) United States Patent (10) Patent No.: US 12,632,111 B2

Miller, III (45) Date of Patent: May 19, 2026

(54) WEARABLE USER MENTAL AND CONTEXTUAL SENSING DEVICE AND SYSTEM

(71) Applicant: Charles Robert Miller, III, Hammond, LA (US)

(72) Inventor: Charles Robert Miller, III, Hammond, LA (US)

( * ) Notice: Subject to any disclaimer, the term of this patent is extended or adjusted under 35 U.S.C. 154(b) by 587 days.

(21) Appl. No.: 16/488,567

(22) PCT Filed: Feb. 23, 2018

(86) PCT No.: PCT/US2018/019571

§ 371 (c)(1),
(2) Date: Aug. 23, 2019

(87) PCT Pub. No.: WO2018/156992

PCT Pub. Date: Aug. 30, 2018

(65) Prior Publication Data

US 2021/0141453 A1 May 13, 2021

Related U.S. Application Data

(60) Provisional application No. 62/462,358, filed on Feb. 23, 2017.

(51) Int. Cl.
G06F 3/01 (2006.01)
A61B 5/00 (2006.01)
(Continued)

(52) U.S. Cl.
CPC ............ G06F 3/015 (2013.01); A61B 5/0075 (2013.01); A61B 5/02055 (2013.01);
(Continued)

(58) Field of Classification Search
CPC .... A61B 2560/0242; A61B 2562/0219; A61B 2562/0223; A61B 2562/0247;
(Continued)

(56) References Cited

U.S. PATENT DOCUMENTS

2005/0113650 A1* 5/2005 Pacione ................ A61B 5/165
600/300
2006/0183980 A1 8/2006 Yang
(Continued)

OTHER PUBLICATIONS

Majumder S, Mondal T, Deen MJ. Wearable Sensors for Remote Health Monitoring. Sensors (Basel). 2017;17(1):130. Published Jan. 12, 2017. doi:10.3390/s17010130 (Year: 2017).*
(Continued)

*Primary Examiner* — Jacqueline Cheng
*Assistant Examiner* — Jonathan E. Cooper

(57) ABSTRACT

A system and method for determining a vector of action based on a psychological state and a contextual state of a user are provided. The system utilizes signals generated by biological processes to determine a user's psychological state and utilizes environmental conditions to determine a user's contextual state. The signals are detected by at least one user sensor within a wearable device, and the environmental conditions are detected by at least one context sensor of the system. The contextual state and psychological state are analyzed to create a vector of action for the user. A vector of action instructs the system to provide the user with an interface action based on the contextual state modified by the psychological state. Because the system continuously determines a user's psychological and contextual states, the system may continuously provide the user with interface actions relevant to the user's current emotional state and environment.

5 Claims, 6 Drawing Sheets

(51) Int. Cl.

| | |
|---|---|
| *A61B 5/0205* | (2006.01) |
| *A61B 5/0531* | (2021.01) |
| *A61B 5/08* | (2006.01) |
| *A61B 5/11* | (2006.01) |
| *A61B 5/16* | (2006.01) |
| *A61B 5/369* | (2021.01) |
| *A61B 5/37* | (2021.01) |
| *A61B 5/374* | (2021.01) |

(52) U.S. Cl.

CPC .......... *A61B 5/0531* (2013.01); *A61B 5/1112* (2013.01); *A61B 5/163* (2017.08); *A61B 5/165* (2013.01); *A61B 5/369* (2021.01); *A61B 5/37* (2021.01); *A61B 5/374* (2021.01); *A61B 5/6802* (2013.01); *A61B 5/08* (2013.01); *A61B 2560/0242* (2013.01); *A61B 2562/0219* (2013.01); *A61B 2562/0223* (2013.01); *A61B 2562/0247* (2013.01); *A61B 2562/0271* (2013.01); *G06F 2203/011* (2013.01)

(58) Field of Classification Search

CPC .......... A61B 2562/0271; A61B 5/0075; A61B 5/02055; A61B 5/02438; A61B 5/0531; A61B 5/055; A61B 5/08; A61B 5/1112; A61B 5/163; A61B 5/165; A61B 5/318; A61B 5/369; A61B 5/37; A61B 5/374; A61B 5/389; A61B 5/6802; A61B 5/6803; A61B 5/6805; G06F 2203/011; G06F 3/011; G06F 3/013; G06F 3/015

See application file for complete search history.

(56) References Cited

U.S. PATENT DOCUMENTS

| | | | | |
|---|---|---|---|---|
| 2007/0238934 | A1 | 10/2007 | Viswanathan | |
| 2008/0177197 | A1 | 7/2008 | Lee et al. | |
| 2009/0264711 | A1* | 10/2009 | Schuler | A61B 5/165 600/300 |
| 2013/0063550 | A1* | 3/2013 | Ritchey | A61B 5/7246 345/207 |
| 2014/0051944 | A1* | 2/2014 | Gillette | A61B 5/02055 600/483 |
| 2014/0107531 | A1 | 4/2014 | Baldwin | |
| 2015/0150074 | A1* | 5/2015 | Nolan | H04L 63/10 726/1 |
| 2015/0320588 | A1* | 11/2015 | Connor | F24F 11/0001 607/104 |
| 2016/0066829 | A1* | 3/2016 | Sales | A61B 5/4076 600/595 |
| 2016/0364002 | A1* | 12/2016 | Gates | G06F 3/017 |
| 2017/0007165 | A1* | 1/2017 | Jain | A61B 5/165 |
| 2017/0316164 | A1* | 11/2017 | Casale | G06N 20/20 |
| 2018/0088903 | A1* | 3/2018 | Mihajlovic | A61B 5/369 |
| 2018/0256432 | A1* | 9/2018 | Mayo | A61H 1/00 |
| 2019/0387998 | A1* | 12/2019 | Garten | A61M 21/00 |

OTHER PUBLICATIONS

Appl. No. PCT/US18/19571, filed Feb. 23, 2018, International Search Report, mailed May 24, 2018.

Appl. No. PCT/US18/19571, filed Feb. 23, 2018, Written Opinion of the International Searching Authority, mailed May 24, 2018.

* cited by examiner

300

305

310

315

400

405

410

600

610

605

615

620

625

139

105

WEARABLE USER MENTAL AND CONTEXTUAL SENSING DEVICE AND SYSTEM

CROSS-REFERENCE TO RELATED APPLICATIONS

This application is a United States National Stage Application of PCT/US18/19571, filed Feb. 23, 2018, which claims priority to U.S. Provisional Patent Application No. 62/462,358, filed Feb. 23, 2017, which applications are incorporated herein by reference.

FIELD OF THE DISCLOSURE

The subject matter of the present disclosure refers generally to a system and method for determining a vector of action based on a psychological state and a contextual state of a user so that an interface action may be assigned.

BACKGROUND

In recent years, computing systems have become increasingly separate from the environment in which they were set up. Personal computers were originally only used in office environments or on factory floors. For many years, the context of use did not change much, and there was little variance in the situations surrounding the computer. Hence, there was no need to adapt to different environments. However, as mobile computing has increasingly become more important, context-aware software has also become more important since it adapts according to the location of use, the collection of nearby people, hosts, and accessible devices. Additionally, context-aware software can make changes to such things over time. A system with these capabilities can examine the computing environment and react to changes to the environment, which has proven to greatly increase the quality of user experience.

Brain-computer interfaces have also become increasingly popular in recent years. Brain-computer interfaces use a direct communication pathway between an enhanced or wired brain and an external device. Currently, many brain control-interfaces rely on discrete measurements of visual evoked potentials gathered from a user while that user matches symbols on a display. These current systems work by combining displays, refresh rates, brainwaves, and visual cortex signals to arrive at a conclusion about what the user was trying to accomplish. Examples of this type of brain-computer interface include keyboard interfaces, in which symbols are displayed on a screen with varying colors, and gaze direction interfaces, in which a user may choose symbols by looking at them as they are displayed in various positions on a screen. This approach works well for special needs patients who are unable to perform basic tasks, such as communication; however, this method lacks the ubiquity that is required for everyday use.

The other major type of brain-control interfaces currently being researched attempt to let the individual user imagine an action such as pull or push, left or right, and up or down. This approach is suboptimal in a commercial environment because not all users think of these discrete actions similarly. From a technical standpoint, it is difficult and time consuming to create a model that works across a population, and from a usability standpoint, a user must train each individual action (pull, push, left, right, up, down, etc.), sometimes for hours or days, to provide useful controls. Additionally, the accuracy of these methods is often in the eighty-percent accuracy range, which is not commercially viable.

Current systems that combine context based computing with brain-control interfaces focus on increasing the accuracy of brain-control interfaces in terms of the context. However, this does not solve the problem that users must train each action for long periods of time since users do not all think alike. Nor does this method result in much of an increase in accuracy over more traditional brain-control interface methods. Should the development of brain-control interface technology continue down this path, one option could be brain implants utilizing such a system, which would drastically reduce adoption by the population.

Accordingly, a need exists in the art for improved systems and methods for determining a vector of action for a user using the user's psychological state and contextual state. Moreover, a need exists in the art for a system and method for assigning interface actions based on the vector of action.

SUMMARY

The present invention provides systems and methods for determining a vector of action based on a psychological state and a contextual state of a user so that an interface action may be assigned, in accordance with the independent claims. Preferred embodiments of the invention are reflected in the dependent claims. The claimed invention can be better understood in view of the embodiments described and illustrated in the present disclosure, viz. in the present specification and drawings. In general, the present disclosure reflects preferred embodiments of the invention. However, some aspects of the disclosed embodiments extend beyond the scope of the claims. To the respect that the disclosed embodiments indeed extend beyond the scope of the claims, the disclosed embodiments are to be considered supplementary background information and do not constitute definitions of the invention per se.

A system and a method for determining a vector of action based on a psychological state and a contextual state of a user so that an interface action may be assigned are provided. The system comprises at least one user sensor secured to a wearable device, at least one context sensor, a processor, and a non-transitory computer readable medium having instructions stored thereon. The at least one user sensor either physically contacts a specific region of the user's body or is positioned adjacent to the user's body without direct contact. When a user wears the wearable device, the at least one user sensor corresponds to a specific region of the user's body and to the underlying biological processes corresponding to that region of the body. As a user performs various actions and/or encounters various circumstances throughout the day while wearing the wearable device, various biological processes undergo continuous changes and produce a signal, which is detected by the at least one user sensor. The system may utilize the signals naturally produced by the biological processes of the user as input to be analyzed to determine a user's psychological state. Thus, the system provides for direct detection of signals generated or produced by biological processes within the body in order to determine the psychological state of the user.

The at least one context sensor may measure an environmental circumstance of the user. An environmental circumstance, or condition, may comprise an external condition, influences on the external conditions, or a condition of time, place, etc. The system may utilize the environmental circumstance data of the user to determine a contextual state of the user. Thus, the system provides for direct detection of the environment in which the user is currently a part of. The processor is operably connected to the at least one user sensor and to the at least one context sensor and is configured to execute operations based on instructions stored on the non-transitory computer readable medium coupled to the processor. The signals detected by the at least one user sensor and the environmental conditions detected by the at least one context sensor may be transmitted and subsequently received by the processor, which may determine an activity level of the biological processes and a contextual state based on the signals and environmental conditions, respectively. The activity level of each biological process measured may be combined into a current epoch array of the user. Based on the current epoch array, the processor may then determine the psychological state of a user.

The system may further comprise a database operably connected to the processor. The database may have a plurality of baseline epochs stored therein, wherein each baseline epoch within the plurality of baseline epochs represents a defined psychological state. Using a machine learning or other similar technique trained on the database, the system may determine a psychological state of a user by comparing the current epoch array to the plurality of baseline epochs. The baseline epoch within the plurality of baseline epochs that most closely resembles the user's current epoch array may correspond to the user's psychological state.

Once the processor has determined the psychological state and the contextual state of the user, the processor may analyze the contextual state in terms of the psychological state. By doing this, the system may create a vector of action. A vector of action may instruct the system to provide the user with an interface action appropriate for the psychological state and the contextual state of the user. An interface action is an action suggested to the user or performed on the user's behalf by the system. Thus, an interface action may be manually carried out by the user or automatically carried out by the system. Because the system is continuously determining a user's psychological state and contextual state, the system may continuously provide the user with interface actions relevant to the user's emotional state and the environment in which the user currently find himself.

Additional features and advantages of the present disclosure will be set forth in the description which follows, and will be apparent from the description, or may be learned by practice of the present disclosure. The foregoing general description and following detailed description are exemplary and explanatory and are intended to provide further explanation of the present disclosure.

DESCRIPTION OF THE DRAWINGS

These and other features, aspects, and advantages of the present disclosure will become better understood with regard to the following description, appended claims, and accompanying drawings where:

DETAILED DESCRIPTION

In the Summary above and in this Detailed Description, and the claims below, and in the accompanying drawings, reference is made to particular features, including method steps, of the invention as claimed. In the present disclosure, many features are described as being optional, e.g. through the use of the verb "may" or the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features, or with all three of the three possible features. It is to be understood that the disclosure in this specification includes all possible combinations of such particular features. For example, where a particular feature is disclosed in the context of a particular aspect or embodiment, or a particular claim, that feature can also be used, to the extent possible, in combination with/or in the context of other particular aspects or embodiments, and generally in the invention as claimed.

The term "comprises" and grammatical equivalents thereof are used herein to mean that other components, steps, etc. are optionally present. For example, a system "comprising" components A, B, and C can contain only components A, B, and C, or can contain not only components A, B, and C, but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

As will be evident from the disclosure provided below, the invention as presently claimed satisfies the need for an improved system and method for creating a vector of action 136 and assigning an interface action 142 based on the user's 105 psychological state 137 and contextual state 138.

Figure 1:
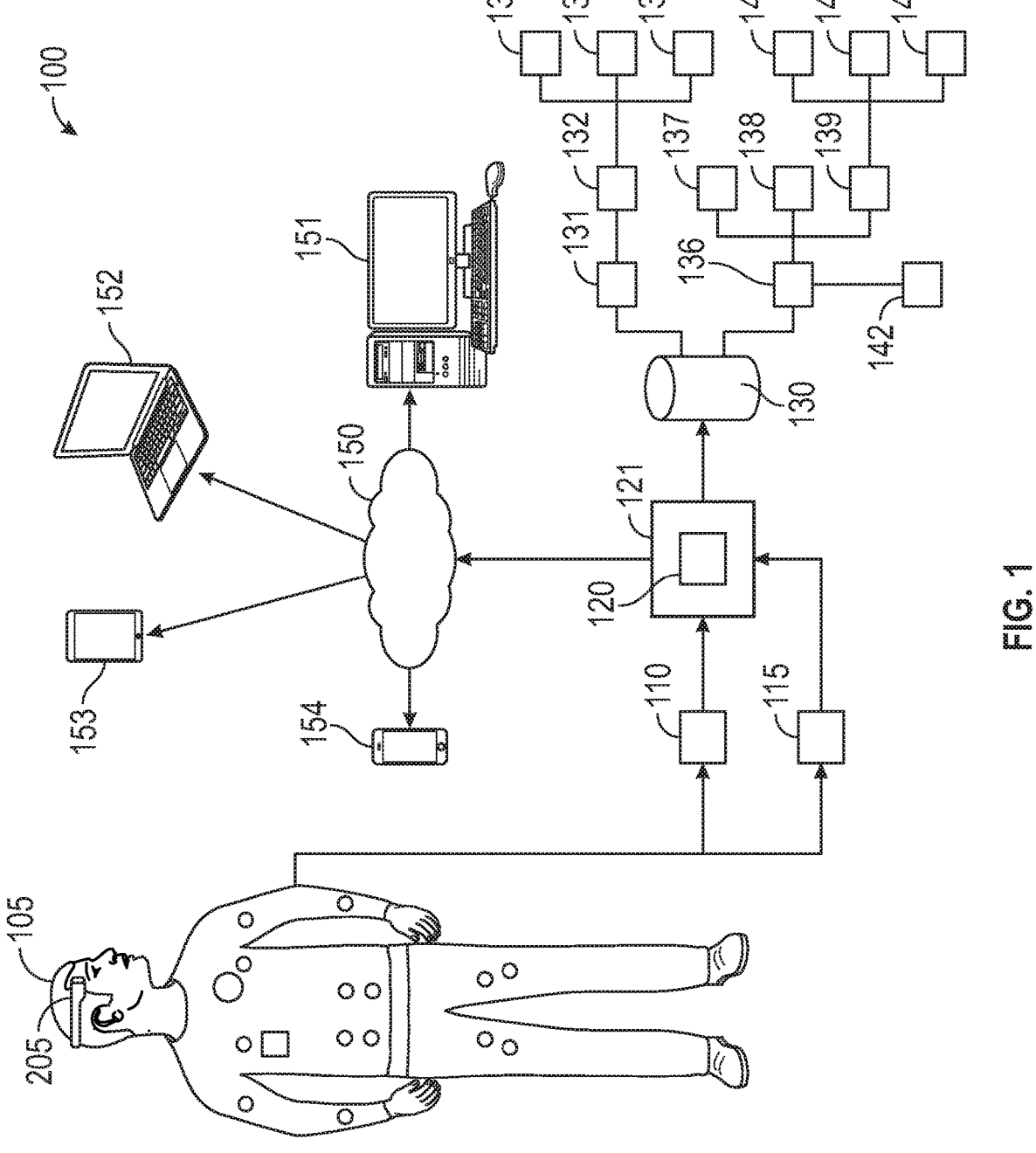
FIG. 1 is a diagram illustrating a system embodying features consistent with the principles of the present disclosure.
Figure 2:
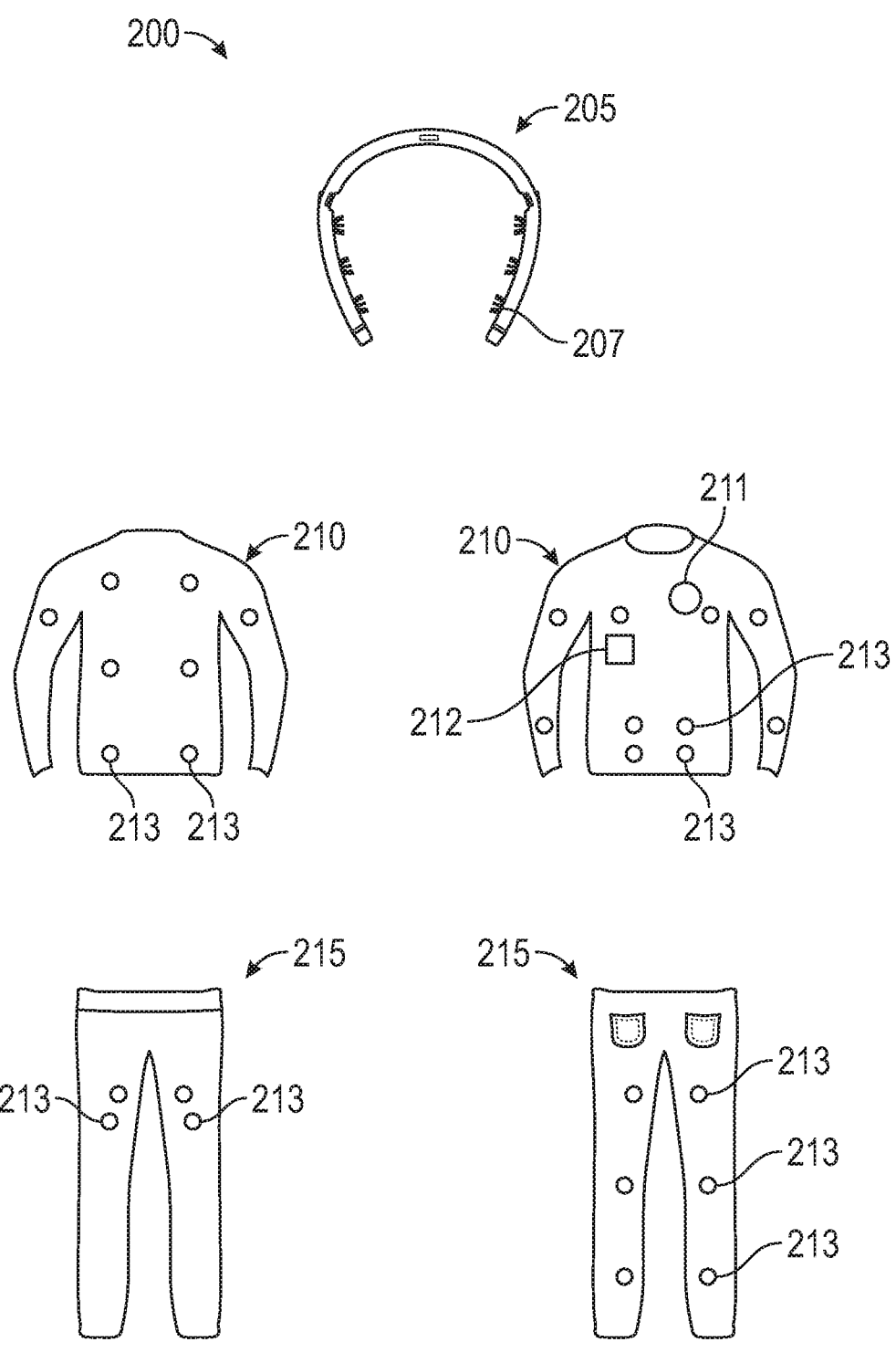
FIG. 2 is a perspective view of example wearable devices in which techniques of the present disclosure may be implemented.
Figure 7:
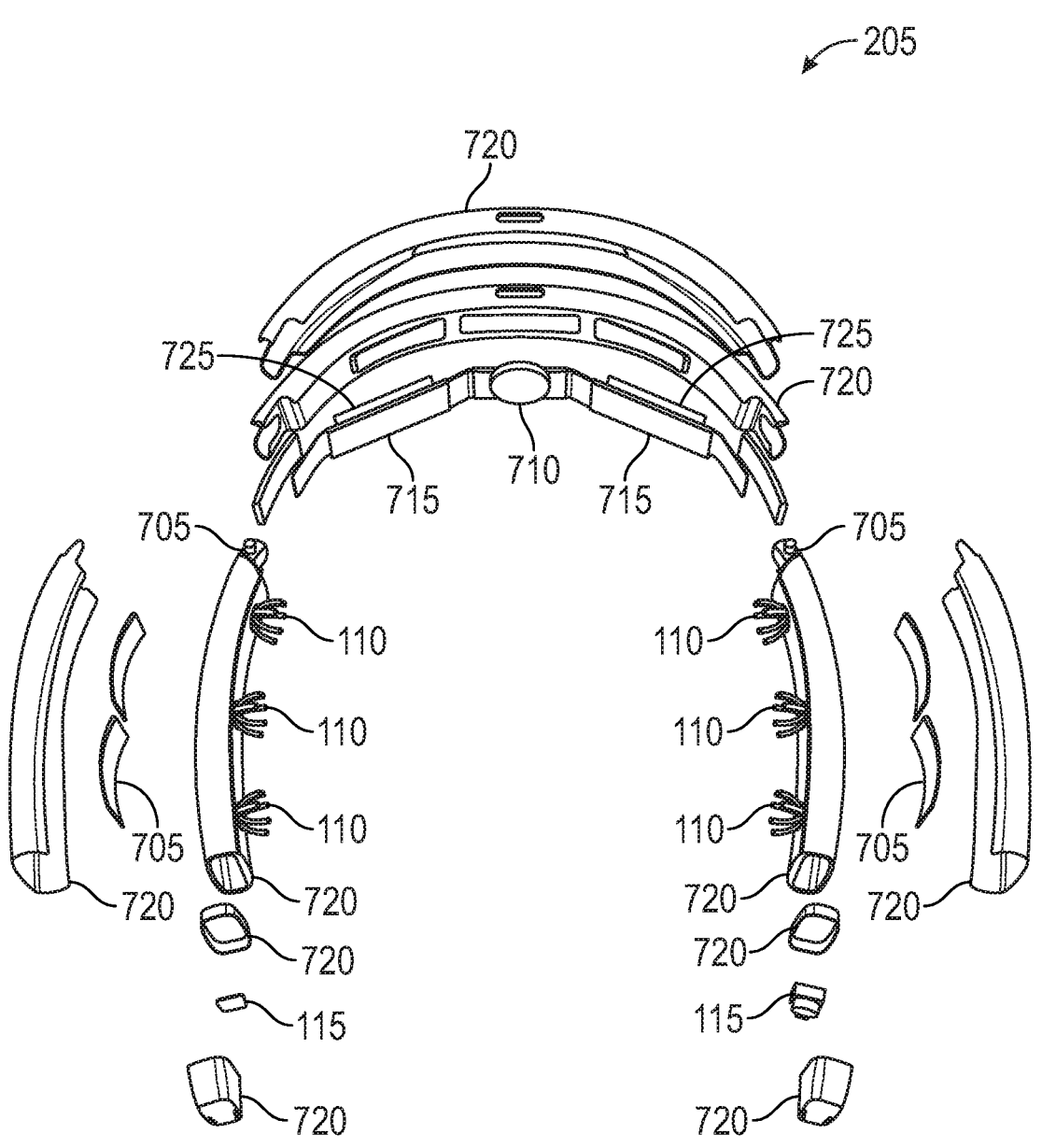
FIG. 7 is an exploded top view of an example wearable device in which techniques of the present disclosure may be implemented.

As illustrated in FIGS. 1, 2, and 7, the system 100 comprises at least one user sensor 110 secured to a wearable device 200, at least one context sensor 115, a processor 121 operably connected to the at least one user sensor 110 and the at least one context sensor 115, and a non-transitory computer readable medium 120 operably connected to the processor 121 and having instructions stored thereon, wherein the instructions instruct the processor 121 to perform specified tasks. The wearable device 200 may be any clothing or equipment that may house sensors. The wearable device 200 may cover all or parts of the head, arms, torso, legs, hands, feet, ankles, wrist, etc. depending on the design of the wearable device 200 and the intended application. The wearable device 200 may be embedded surgically insider the user's body. In some embodiments, a wearable device 200 worn on the head may cover only the portion of the head necessary for the intended application of measuring brainwaves. For instance, a wearable device 200 worn on the chest may cover only the portion of the chest necessary for the intended purpose of measuring heart rhythm. In another illustrative example, a wearable device 200 worn on the wrist may cover only part of the wrist necessary for the intended application of measuring a pulse.

The at least one user sensor 110 may be secured within the wearable device 200 in a way such that when the wearable device 200 is worn, the at least one user sensor 110 may measure a signal produced by a biological process. In this embodiment, the biological process measured depends on the type of sensor. In an embodiment, the at least one user sensor 110 may measure a cognitive process or a physical process. For instance, an at least one user sensor 110 comprising an electroencephalogram may measure a cognitive process, such as electrical activity in the brain related to brainwaves. For instance, an at least one user sensor 110 comprising an electromyogram may measure a physical process, such as an electric potential generated during a muscle movement. Types of sensors that may be used as an at least one user sensor 110 include, but are not limited to, electroencephalogram (EEG), electromyogram (EMG), electrocardiogram (ECG), electrocorticography (ECoG), electrodermal activity (EDA), functional near infrared spectroscopy (NIR), infrared spectroscopy machine (IR), temperature, microphone, and eye tracking.

As shown in FIGS. 1, 2, and 7, the at least one user sensor 110 may be secured within the wearable device 200 such that when the wearable device 200 is donned by a user 105, each sensor of the at least one user sensor 110 may correspond to a region of the body typically used for measuring a specific biological process. For instance, an at least one user sensor 110 comprising an EEG sensor 207 may be oriented within the wearable device 200 such that when a user 105 is wearing the wearable device 200, the EEG sensor 207 may make contact with the user's 105 head area near the brain. In another example embodiment, an at least one user sensor 110 comprising an ECG sensor 211 may be oriented within the wearable device 200 such that when a user 105 is wearing the wearable device 200, the ECG sensor 211 may make contact with the user's 105 chest area near the heart. In another example embodiment, an at least one user sensor 110 comprising a breath meter 212 may be oriented within the wearable device 200 such that when a user 105 is wearing the wearable device 200, the breath meter 212 may make contact with the user's 105 chest area near the lungs. In another example embodiment, an at least one user sensor 110 comprising an EMG sensor 213 may be oriented within the wearable device 200 such that when a user 105 is wearing the wearable device 200, the EMG sensor 213 may make contact with a desired muscle area of the user 105. The at least one user sensor 110 may physically contact a user's 105 skin when the wearable device 200 is worn. Alternatively, the at least one user sensor 110 may be a non-contact sensor positioned adjacent to a user's body without direct contact with the user's skin when the wearable device 200 is worn.

FIGS. 1, 2, and 7 illustrate examples configurations of the at least one user sensor 110 within a number of wearable devices 205, 210, 215. The number of at least one user sensors 110 and the orientation of the at least one user sensors 110 within a wearable device 200 may vary from application to application or based on the dimensions or design of the wearable device 200. In an embodiment shown in FIGS. 1, 2, and 7, the wearable device 200 may comprise a number of pronged EEG sensors designed to make contact with a user's 105 head area. In an embodiment shown in FIGS. 1 and 2, the wearable device 200 may comprise a number of EMG, ECG, and breath sensors designed to make contact with a user's 105 torso and leg areas. In a preferred embodiment, at least one user sensor 110 may be secured within the wearable device 200 at the time of the wearable device's 200 manufacture such that at least one user sensor 110 or at least one context sensor 115 may be pre-installed within the wearable device 200, as shown in FIGS. 1, 2, and 7. Alternatively, at least one user sensor 110 may be installed later as an add-on device, or a component thereof, configured to retrofit an existing wearable device 200.

At least one context sensor 115 may be secured within the wearable device 200 in a way such that when the wearable device 200 is donned by a user 105, each sensor may accurately observe an environmental condition of the user 105. In this way, the wearable device 200 may measure an environmental circumstance of a user 105 and transmit the environmental circumstance data to the processor 121. The processor 121 may then analyze the environmental circumstance data to determine a contextual state of the user 105. For instance, at least one context sensor 115 comprising a GPS may measure geospatial data of a user 105 and subsequently transfer the geospatial data to the processor 121. The processor 121 may then determine the user's 105 geospatial location based on this environmental circumstance data. In another example embodiment, at least one context sensor 115 comprising a microphone may measure sound data of a user 105 and subsequently transfer that data to the processor 121. The processor 121 may then, for instance, determine whether the user 105 is indoors or outdoors. In another example embodiment, at least one context sensor 115 comprising a camera may measure visual data of a user 105 and subsequently transfer the visual data to the processor 121. The processor 121 may then, for instance, determine whether the user 105 is walking or riding in a vehicle. In one embodiment, the environmental circumstance data may be analyzed using a machine learning technique.

The wearable device 200 may be configured to securely conform to a user's 105 body in a way such that the at least one user sensor 110 may firmly contact a user's 105 skin. For instance, the wearable device 200 may be molded in the shape of a user's 105 body. For instance, the wearable device 200 may be made of a flexible material having a property that may allow the flexible material to conform to a user's 105 body. For instance, the wearable device 200 may be comprised of a series of rigid members dispersed within or attached to a flexible material, wherein the flexible material conforming to a general shape may force the rigid members to conform to a general shape. In an embodiment shown in FIG. 7, the wearable device 200 may have a number of rigid hinges 705 that generally shape a semi-flexible polymer material in a way such that the wearable device 200 may conform to the user's 105 head by causing the ends of the wearable device 200 to articulate towards one another.

The wearable device 200 may also have an adjustment mechanism 710, wherein the adjustment mechanism 710 may allow a user 105 to increase or decrease the size of the wearable device 200. For instance, the wearable device 200 may comprise a clasp that may fasten to a strap, wherein, depending on the location of the clasp in relation to the strap, the size of the wearable device 200 may be increased or decreased. For instance, the wearable device 200 may comprise a knob and at least one gear connected to the wearable device 200, wherein the knob may be connected to the gear in a way such that turning the knob may cause the at least one gear to engage the wearable device 200 in a way such that the size of the wearable device 200 may be increased or decreased. In an embodiment shown in FIG. 7, a knob allows a user 105 to increase or decrease the circumference of the wearable device 200 so that the wearable device 200 may more securely fit the user's 105 head. By allowing the user 105 to adjust the size of the wearable device 200, the at least one user sensor 110 may make stronger contact with the user's 105 body, increasing the effectiveness of the at least one user sensor 110, and may allow the at least one context sensor 115 to more consistently record a user's environmental conditions. In an embodiment shown in FIG. 7, by allowing the user 105 to adjust the size of the wearable device 200, the user 105 may better secure the wearable device to the user's 105 head, which allows the at least one user sensor 110 to better contact the user's 105 head, and places the at least one context sensor 115 of the wearable device 200 in a position to gather environmental circumstance data from a first-person point of view. Thus, the user 105 may increase the accuracy in which the system may determine the user's contextual state 138 and psychological state 137.

The circuitry 715 that may connect the processor 121, the at least one user sensor 110, the at least one context sensor 115, and the non-transitory computer readable medium 120, may comprise a printed circuit board (PCB) or a flexible circuit (FPC), but is not limited to these types of circuits. In an embodiment shown in FIG. 7, the wearable device 200 may comprise a combination of PCBs and FPCs so that a user 105 may adjust the size of the wearable device 200 without harming any of the circuitry 715. The wearable device 200 may have a power supply 725 so that the processor 121, the at least one user sensor 110, the at least one context sensor 115, and the non-transitory computer readable medium 120, may receive power without the need to be near a power source. In an embodiment shown in FIG. 7, the wearable device may have a battery for powering the wearable device 200 when the user 105 is not near a power source.

The wearable device 200 may have an encasing 720 to protect the processor 121, the at least one user sensor 110, the at least one context sensor 115, and the at least one non-transitory computer readable medium 120. For instance, a wearable device 200 may have a rigid encasing to protect the internal components of the wearable device 200 from impacts. For instance, the wearable device may have a semi-flexible encasing to protect the wearable device 200 from impacts and allow flexibility. In an embodiment shown in FIG. 7, the encasing 720 may be made of a semi-flexible material such as a semi-flexible polymer, which may protect the wearable device 200 from impacts while allowing the wearable device 200 to conform to a user's 105 head. For instance, the encasing 720 may be a soft encasing made of a flexible material such as a rubber. In an embodiment shown in FIG. 7, the wearable device 200 may comprise a soft encasing made of a fabric to provide the wearable device 200 with scratch protection and allow the user 105 to customize the wearable device 200.

As a user 105 performs various actions and/or encounters various circumstances throughout the day while wearing the wearable device 200, various biological processes may undergo continuous changes and produce a signal. The system 100 utilizes the signals naturally produced by the biological processes of the user 105 as input to be analyzed to determine a user's 105 psychological state 137. Thus, the at least one user sensor 110 may be configured to detect signals generated or produced by biological processes within the region of the user's 105 body to which the at least one user sensor 110 corresponds. In one embodiment, detection of such signals may be performed by measuring the potential difference (voltage difference) between two or more electrodes of the at least one user sensor 110.

The at least one user sensor 110 may be operably connected to the processor 121 in a way such that the signals may be transmitted from at least one user sensor 110 to the processor 121. At least one user sensor 110 may be operably connected to the processor 121 via a physical connection between at least one user sensor 110 and the processor 121. Alternatively, at least one user sensor 110 may be wirelessly connected to the processor 121. For instance, to physically connect the at least one user sensor 110 to the processor 121, wiring suitable for transmitting signals may extend from at least one user sensor 110 to the processor 121. At least one user sensor 110 may be individually wired and operably connected to the processor 121 or a single wire may connect multiple user sensors 110 to the processor 121. Conduit may be used to protect the wiring. In one embodiment, as depicted in FIG. 7, signal processing circuitry may be used for operably connecting at least one user sensor 110 to the processor 121. A wireless connection may be established via Bluetooth or similar wireless technology configured to wirelessly connect two devices such that information or signals may be exchanged from one device to another.

The processor 121 is configured to perform the operations disclosed herein based on instructions stored within the system 100. The processor 121 may be any processor or microprocessor suitable for executing instructions. In some embodiments, the processor 121 may have a memory device therein or coupled thereto suitable for storing the data, content, or other information or material disclosed herein. In some instances, the processor 121 may be a component of a larger computing device. A computing device that may house the processor 121 therein may include, but are not limited to, laptops, desktops, workstations, personal digital assistants, servers, mainframes, cellular telephones, tablet computers, or any other similar device. Accordingly, the inventive subject matter disclosed herein, in full or in part, may be implemented or utilized in devices including, but not limited to, laptops, desktops, workstations, personal digital assistants, servers, mainframes, cellular telephones, tablet computers, or any other similar device.

The instructions may be stored on a non-transitory computer readable medium 120 that may be coupled to the processor 121, as shown in FIG. 1. Alternatively, the instructions may be stored or included within the processor 121. Examples of non-transitory computer readable mediums may include, but are not limited to, magnetic media such as hard disks, floppy disks, and magnetic tape; optical media such as CD ROM discs and DVDs; magneto-optical media such as optical discs; and hardware devices that are specially configured to store and perform instructions, such as read-only memory (ROM), random access memory (RAM), or flash memory. The described hardware devices may be configured to act as one or more software modules in order to perform the operations disclosed herein.

Upon execution of the appropriate instructions, the processor 121 may receive signals transmitted by at least one user sensor 110 and subsequently determine a psychological state 137 of the user 105. The signals received by the at least one user sensor 110 may be indicative of muscle movement, brain activity, heart rhythm, breath rate, pulse, etc. of a user

105, depending on the biological process for which the at least one user sensor 110 corresponds. The activity level of each biological process may be determined, at least in part, by signals detected by the at least one user sensor 110 and then transmitted to the processor 121.

Depending on the application, various aspects of the signals transmitted by the at least one user sensor 110 may be processed by the processor 121 to determine the activity level of a biological process. For instance, the processor 121 may determine the activity level of a biological process based on the presence or absence of a signal, voltage, frequency, or other indicia of the signal transmitted by the at least one user sensor 110. The activity level of biological processes may also be based, at least in part, on the position of the sensor within the wearable device 200. Before analyzing the signals transmitted by the at least one user sensor 110 to determine the psychological state 137 of the user 105, the signals may be processed by the processor 121 to determine overall power of the signal, mean deviation of brain waves, sinusoidal oscillations, noise reduction, topological distribution across the scalp, discrete and continuous waveforms, Morlet wavelets, event related potentials, principal components, independent components, single mathematical dipoles, source localization, phase synchrony, power correlations, Spearman coefficients, Pearson coefficients, entropy, differential entropy, univariate/bivariate auto regression, granger predictions, and other forms of bio signal analysis, or any combination thereof.

In one embodiment, the system 100 of the present disclosure may use intra-sensor data sampling to determine the activity level of a biological process. To facilitate intra-sensor data sampling, the system 100 may have two or more user sensors 110 with the same intended application. In addition, the wearable device 200 housing the two or more user sensors 110, the processor 121 operably connected to the two or more user sensors 110, and the non-transitory computer readable medium 120 operably connected to the processor 121 and having instructions stored thereon, may be configured such that any of the user sensors 110 may be compared to any other of the user sensors 110 within the wearable device 200, depending on the design of the wearable device 200 and the intended application of the sensor. Thus, a signal detected by one user sensor 110 within the wearable device 200 may be compared to other similar signals detected by other similar sensors within the wearable device 200. Thus, by using other similar signals detected by other user sensors 110 within the wearable device 200 as comparative metrics, the processor 121 may determine the strength of a particular signal. Because each signal may be detected by similar user sensors 110 and each user sensor 110 may measure a similar biological process, the strength of signals may be used to determine an activity level of a biological process through intra-sensor data sampling. In one embodiment, the strength of the signals or the activity level of the biological processes to which such signals correspond may be stored within the system 100 or transferred by the processor 121 to a database 130 via a network.

Once the activity level of the biological processes has been determined by the processor 121, the activity levels of the biological processes may be combined to form a current epoch array of a user 105. Therefore, the current epoch array of a user 105 may comprise biological process data pertaining to one or more biological processes measured by at least one user sensor 110 housed in a wearable device 200. For instance, a user 105 wearing a wearable device 200 having at least one user sensor 110 measuring muscle movement, heart rhythm, and breath rate may have a current epoch array comprising muscle movement, heart rhythm, and breath rate. The current epoch array may also comprise fewer biological processes than may be measured by the at least one user sensor 110 secured within a wearable device 200. For instance, a user 105 wearing a wearable device 200 having at least one user sensor 110 measuring muscle movement, heart rhythm, and breathing rate may have a current epoch array comprising breathing rate. Additionally, a current epoch array may comprise biological processes data measured by user sensors 110 in more than one wearable device 200. For instance, a user 105 wearing a wearable device 200 having at least one user sensor 110 for measuring brainwaves and another wearable device 200 having at least one user sensor 110 for measuring pulse may have a current epoch array comprising pulse and brainwave data. Therefore, the current epoch array of a user 105 may comprise activity levels of one or more biological processes measured by at least one user sensor 110 of one or more wearable devices 200.

To determine the psychological state of a user 105, the current epoch array may be analyzed by the processor 121. The system may determine a user's psychological state continuously or at a set rate of time. In one embodiment, the processor 121 may compare the current epoch array of the user 105 with biological process threshold data. The biological process threshold data may correspond to a defined psychological state 137. Biological process threshold data from multiple biological processes may be combined together to create a baseline epoch 132. The processor 121 may compare the current epoch array of a user 105 to a plurality of baseline epochs 131 to determine the psychological state 137 of a user 105. In one embodiment, the baseline epoch 132 that most closely resembles the current epoch array of the user 105 may correspond to the psychological state 137 of the user 105. Accordingly, a current epoch array may resemble more than one baseline epoch 132 within the plurality of baseline epochs 131, but only the baseline epoch 132 that most closely matches the current epoch array will determine a user's 105 psychological state 137. A user 105 may save a current epoch array and link that current epoch array with a psychological state 137. In this way, the user 105 may create a custom baseline epoch and personalize the system 100. The processor 121 may then compare the user's 105 current epoch array to the plurality of baseline epochs 131 and custom baseline epochs to determine the user's 105 psychological state 137. In one embodiment, the psychological state 137 may be determined using a machine learning technique.

A psychological state 137 may comprise, but is not limited to, the following emotions: awe, surprise, calm, joy, euphoria, enlightenment, anger, confusion, clarity, satisfaction, love, jealousy, sadness, frustration, excited, epiphany, and amped up. The emotions may be defined by biological signals including, but not limited to, brainwave activity, pulse, heart rhythm, breathing rate, etc., or any combination thereof. In another embodiment, the psychological state 137 may be defined in terms of or modified by a cortical state, wherein a cortical state refers to the current subthreshold membrane potential change of the user's 105 neurons. Generally, this cortical state may refer to an up state or a down state of neurons, wherein a neuron in a down state is hyperpolarized and a neuron in an up state is depolarized. Because neurons are constantly changing between up states and down states, depending on the environmental conditions of the user 105, the system may determine the psychological state 137 of the user 105 based on the neural activity.

Figure 3:
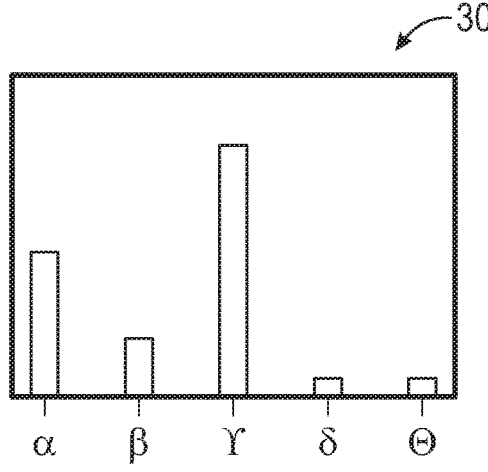
FIG. 3 is an example of a current epoch array embodying features consistent with the principles of the present disclosure.
Figure 3:
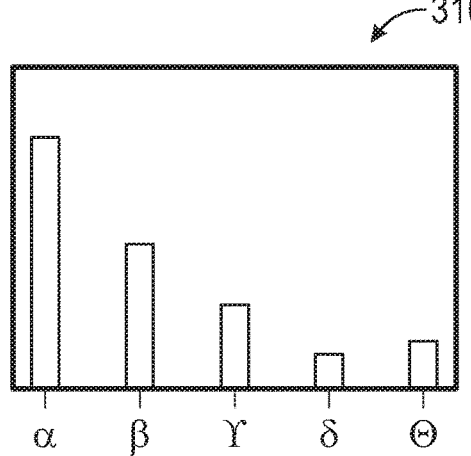
Figure 3:
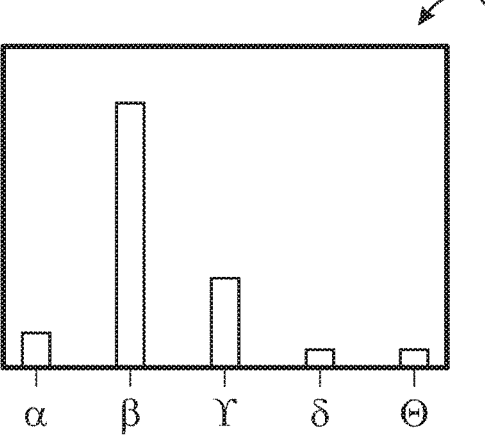
Figure 4:
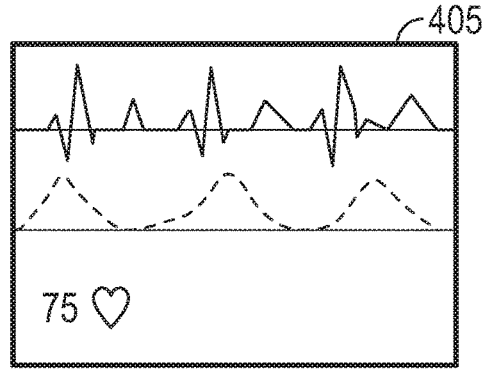
FIG. 4 is an example of a current epoch array embodying features consistent with the principles of the present disclosure.
Figure 4:
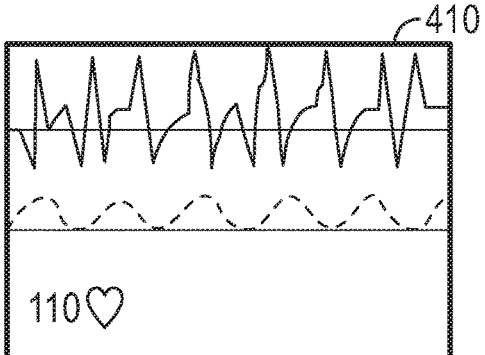

As shown in FIG. 1, the system 100 may further comprise a database 130 operably connected to the processor 121. The database 130 may store a plurality of baseline epochs 131 therein, wherein each baseline epoch 132 of the plurality of baseline epochs 131 may be indicative of a psychological state 137 of a user 105, such as the example baseline epochs 300 and 400 illustrated in FIGS. 3 and 4. The database may store baseline epochs 132 comprising biological process threshold data of a single biological process as well as baseline epochs 132 comprising biological process threshold data of multiple biological processes. For instance, one baseline epoch 132, as illustrated by 305, 310, and 315, may be indicative of a psychological state 137 in terms of EEG waves 133, whereas another baseline epoch 132, as illustrate by 405 and 410, may be indicative of a psychological state 137 in terms of pulse, heart rhythm 134, and breathing rate 135. Thus, the system 100 may detect one or more biological processes of a user 105 and transform that data into a psychological state 137 of the user 105 by comparing the current epoch array of the user 105 to a plurality of baseline epochs 131 and selecting the baseline epoch 132 that most closely resembles the current epoch array.

At least one context sensor 115 may measure an environmental circumstance of the user 105. An environmental circumstance may comprise a location of use, the collection of nearby people, hosts, accessible devices, external conditions, influences on the external conditions, and others circumstances. Types of sensors that may be used as a context sensor 115 may include, but are not limited to, a microphone, camera, gyroscope, accelerometer, magnetometer, pressure sensor, temperature sensor, gas sensor, eye tracking sensor, global positioning system, triangulation sensor, time-of-flight sensor, pedometer, respiratory sensor, and service application, or any combination thereof.

Once the psychological state 137 and the contextual state 138 have been determined, the processor 121 may analyze the contextual state 138 in terms of the psychological state 137 to determine a vector of action 136. A vector of action 136 may instruct the system 100 to provide the user 105 with an interface action 142 based on the contextual state 138 modified by the psychological state 137. The interface action 142 may be automatic such that the system 100 may perform the interface action 142 without the user 105 having to provide an input. Alternatively, the interface action 142 may be manual such that a user 105 may select the interface action 142 from a list of interface actions before the interface action 142 may be performed. The system 100 may present an interface action 142 to the user 105 via a display 151, 152, 153, 154 operably connected to the processor 121 via a network 150, and the user 105 may select an interface action 142 from the display 151, 152, 153, 154. Displays 151, 152, 153, 154 may include, but are not limited to, visual, auditory, cutaneous, kinesthetic, olfactory, and gustatory, or any combination thereof.

An interface action 142 may include, but is not limited to, a device action and a logging action. A device action may refer to an action performed by a device operably connected to the system 100. Devices that may perform a device action may include, but are not limited to, cameras, video recorders, microphones, GPS, televisions, phones, computing devices, and applications. Logging actions may refer to the saving of data received by and transmitted from the processor 121 on the non-transitory computer readable medium 120 or a database 130 operably connected to the processor 121. For instance, a current epoch array, the contextual state 138, and the interface actions 142 recommended to the user 105 may be saved by the system 100. In one embodiment, the current epoch array, contextual state 138, and interface actions 142 recommended to the user 105 may be saved as an impact moment, wherein the impact moment may be further analyzed by the system 100 to further understand the psychological state 137 in terms of the contextual state 138.

For instance, the system 100 worn by a user 105 may determine that the user 105 may be in a psychological state 137 of awe, surprise, calm, joy, euphoria, enlightenment, or others, based on the user's 105 current epoch array. The system 100 may be fixed to perform a device action of taking a picture, recording a variably timed video, recording audio for a variable amount of time, recording a video for the duration of the psychological state 137, recording audio for the duration of the psychological state 137, and recording measurements, such as geospatial data, time, and temperature, whenever it may be determined that a user 105 has a certain psychological state 137. The system 100 may then perform a logging action by saving the current epoch array of the user 105, the contextual state 138, and the interface actions 142 on the non-transitory computer readable medium 120 or on a database 130 operably connected to the processor 121 as a logged current epoch array 140, logged contextual state 141, and logged interface action 143. The combination of logged interface action 143, the logged current epoch array 140, and the logged contextual state 141 may be saved as an impact moment, which may be analyzed by the system 100 to recommend more personalized services, products, and applications.

By analyzing impact moments, the system 100 creates a contextual-cortical driver 139, wherein a contextual-cortical driver 139 may be defined as a commonality between a contextual state 138 and a psychological state 137. In one embodiment, the impact moment may be analyzed using a machine learning technique, such as artificial intelligence. Contextual-cortical drivers 139 may be saved in the non-transitory computer readable medium 120 or in a database 130 operably connected to the processor 121. Once a contextual-cortical driver 139 is created, the system 100 may use the contextual-cortical driver 139 to create a more personalized vector of action 136, which may provide the user 105 with more personalized interface actions 142. For instance, if a user 105 commonly has a psychological state 137 of awe, surprise, calm, joy, euphoria, enlightenment, or others, in buildings and restaurants with exposed wood architecture, a contextual-cortical driver 139 may be identified as architecture for that particular psychological state 137. The system 100 may then recommend similar architectural locations to visit or patron in the course of the user's 105 travel or daily life. Alternatively, by analyzing multiple impact moments and determining that it may be multiple types of architecture instead of a specific expression of architecture that causes the user 105 to experience a particular psychological state 137, the system 100 may determine that a contextual-cortical driver 139 of the user 105 may be observing architecture in general.

Because the system 100 may create multiple contextual-cortical drivers for a user 105, the system 100 may increasingly personalize the vector of action 136 to provide the user 105 with more personalized interface actions 142. For instance, a user 105 may have a contextual-cortical driver 139 involving a psychological state 137 indicative of an "epiphany" while reading, watching a movie, listening to music, etc. When this circumstance occurs, the system 100 may enact an interface action 142 that records a picture, video, audio, URL, or highlights e-book text so the "epiphany" moment may be projected back to the user 105 at a later time. In another example, a user 105 may have a contextual-cortical driver 139 involving a psychological state 137 indicative of "satisfaction" while visiting a restaurant, coffee shop, art gallery, etc. When this circumstance occurs, the system 100 may recommend an interface action 142 of rating or sharing feelings about the establishment or experience. In another example, a user 105 may have a contextual-cortical driver 139 involving a psychological state 137 of "intense interest" when reading a book, watching a movie, engaging in conversation, etc. When this circumstance occurs, the system 100 may enact an interface action 142 to modify the user's 105 environment to enhance the user's 105 experience. The modification of the user's 105 environment may include, but is not limited to, changing lighting, turning off devices, adjusting music volume, and silencing notifications on a mobile device, or combinations thereof.

For instance, a user 105 may have a contextual-cortical driver 139 involving a psychological state 137 of "amped up" when listening to music with a particular chord progression or beats per minute. A user 105 may be able to select music based on the psychological state 137, rather than genre or artist, and play music with chord progressions and beats per minute associated with the psychological state 137. In another example, a user 105 may have a contextual-cortical driver 139 involving a psychological state 137 of "confusion" when traveling in an unfamiliar area or to an unfamiliar location. When this circumstance occurs, the system 100 may enact an interface action 142 that engages devices operably connected to the system 100 to outline a path in front of the user 105 or on a map that guides the user 105 to the nearest geolocation in which the user 105 experienced a psychological state 137 of "clarity." In another example, a user 105 may have a contextual-cortical driver 139 involving any psychological state 137 when a user 105 may be creating art in a non-physical medium. When this circumstance occurs, the system 100 may enact an interface action 142 to ask a user 105 whether they would like to modify the art created in the non-physical medium based on the user's 105 psychological state 137. Types of modification may include, but is not limited to, a red hue when in a psychological state 137 of "angry" or a blue hue when in a psychological state 137 of "joy."

Figure 6:
FIG. 6 is a diagram illustrating a system embodying features consistent with the principles of the present disclosure.
Figure 6:
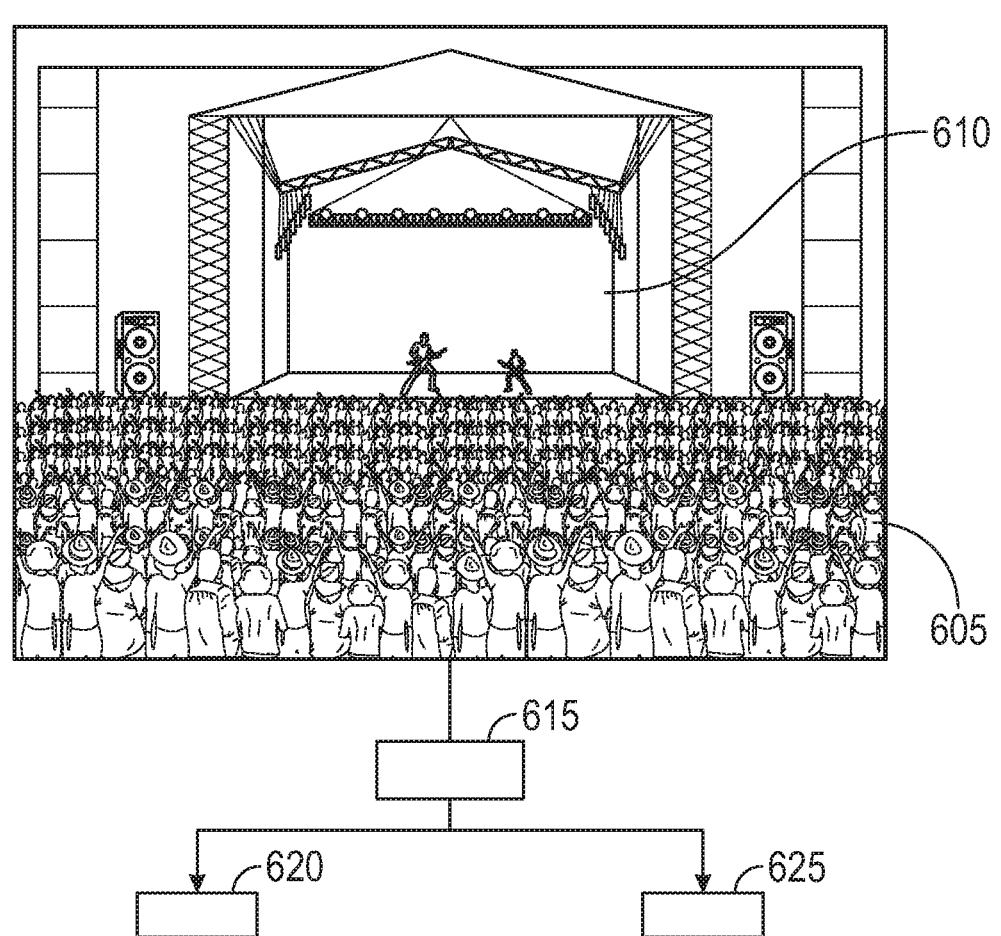
Figure 6:
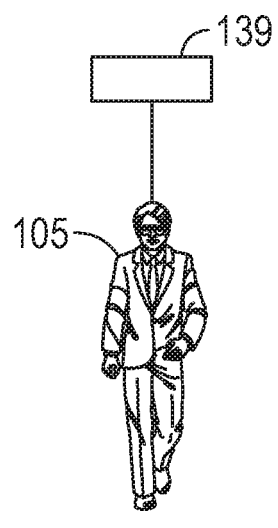

As shown in FIG. 6, the system 100 may also be used to create a group of contextual-cortical drivers 615 based on a group psychological state 620 and a group contextual state 625 of a group of users 605 participating in a group activity 610 set in a particular geolocation 600. This may be done by creating an average current epoch array for the group of users that corresponds to a group psychological state 620 for the group of users 605 and an average environmental condition for the group of users 605 that corresponds to a group contextual state 625 for the group of users 605. A group activity 610 may include, but is not limited to, a live music event, protest, political rally, art gallery showing, and other events or activities in which groups of people may be common. When a group of contextual-cortical drivers 615 is created, the system 100 may recommend other users 105 to participate in the group activity 610 based on whether the other users' 105 contextual-cortical drivers 139 match the group of contextual-cortical drivers 615. For instance, a group of users 605 participating in a group activity 610 at a particular geolocation may have a group of contextual-cortical driver 615 involving a group psychological state 620 of "excited" while participating in that group activity 610. A user 105 not participating in the group activity 610 at that particular geolocation may have a contextual-cortical driver 139 similar to the group context cortical driver when participating in that group activity 610, and the system 100 may enact an interface action that recommends that the user 105 participate in the group activity 610.

The system 100 may also be used to help determine how well a user 105 or group of users 605 understand material in a learning environment. Alternatively, the system 100 may provide suggestions to a user 105 teaching the material to another user 105 or a group of users 605 so that the material may be taught in the most effective manner. For instance, a group of users 605 may have a group of contextual-cortical drivers 615 involving a group psychological state 620 of "frustration" while learning a particular piece of material. When this circumstance occurs, the system 100 may enact an interface action 142 recommending that a user 105 attempting to teach the material to the group of users 605 take a different approach to teaching the material than the method being used. The system 100 may also be used to determine a particular time and place in which a user 105 or group of users 605 may be able to best understand a particular piece of material. For instance, a group of users 605 may have a group of contextual-cortical drivers 615 involving a group psychological state 620 of "concentrating" after taking a nap. When this circumstance occurs, the system 100 may enact an interface action 142 recommending that a user 105 attempting to teach the material to the group of users 605 explain the most difficult material during this time. As the system 100 creates more contextual-cortical drivers 139 for a user 105 and more group of contextual-cortical drivers 615 for a group of users 605, the system 100 may allow users 105 to personalize learning environments so that a user 105 or group of users 605 may be taught material in the most effective way possible.

The present disclosure is further directed to a method for determining a vector of action 136 so that an interface action 142 may be assigned. More specifically, a method for assigning interface actions 142 based on a user's 105 psychological state 137 and contextual state 138 is provided. The present methodology may utilize a system 100 having some or all of the features consistent with the embodiments previously disclosed for the system 100 for determining a vector of action 136 to execute certain steps for certain method steps disclosed herein. A system 100 comprising a wearable device 200 having at least one user sensor 110 and at least one context sensor 115 secured therein, a processor 121 operably connected to the at least one user sensor 110, and the at least one context sensor 115, and a non-transitory computer readable medium 120 having instructions stored thereon and operably connected to the processor 121, is used to execute certain steps of the method.

Figure 5:
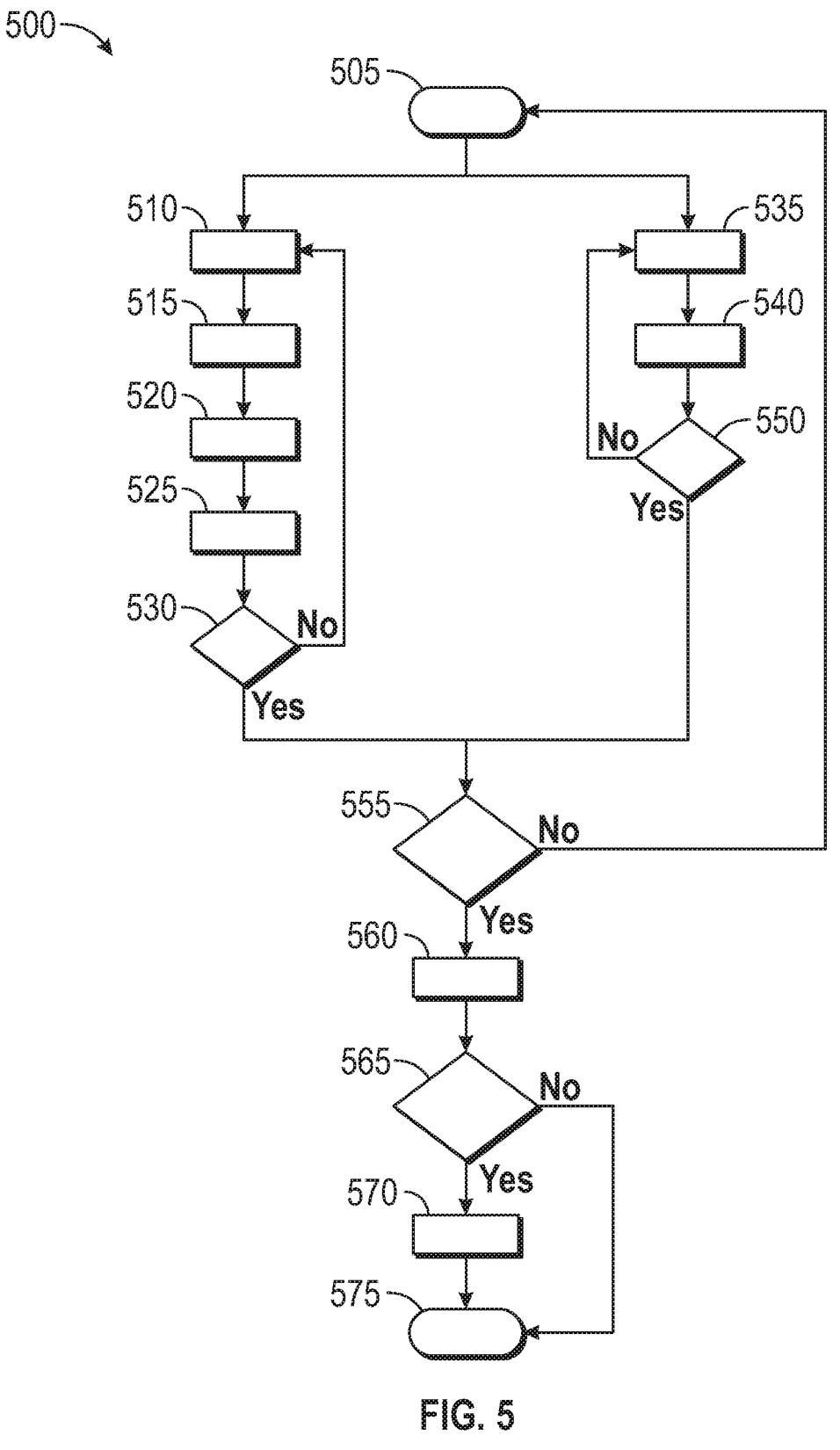
FIG. 5 is a flow chart illustrating a method for determining a vector of action so that an interface action may be assigned consistent with the principles of the present disclosure.

FIG. 5 illustrates a flow chart 500 showing method steps that may be carried out to create a vector of action 136 and subsequently assign an interface action 142. Before the method steps may be carried out, a wearable device 200 having at least one user sensor 110 and at least one context sensor 115 secured therein is donned by a user 105 and secured to the user 105 in a way such that the at least one user sensor 110 may detect biological processes of the user 105 and the at least one context sensor 115 may sense an environmental condition of the user 105. Step 505 indicates the beginning of the method for determining a vector of action 136 so that an interface action may be assigned to a user 105. During the biological process detection step 510, the at least one user sensor 110 may detect signals produced by a biological process of the user 105. The at least one user sensor 110 may detect biological processes such as brainwaves, muscle contractions, heart rate, etc.

When signals produced by biological processes are detected by the at least one user sensor 110, the signals may be transmitted to the processor 121 during the biological process transmission step 515. Once the processor 121 receives the biological process data, the processor 121 may perform instructions stored on the non-transitory computer readable medium 120 that instruct the processor 121 to determine overall power of the signal, mean deviation of brain waves, sinusoidal oscillations, noise reduction, topological distribution across the scalp, discrete and continuous waveforms, Morlet wavelets, event related potentials, principal components, independent components, single mathematical dipoles, source localization, phase synchrony, power correlations, Spearman coefficients, Pearson coefficients, entropy, differential entropy, univariate/bivariate auto regression, granger predictions, and other biosignal analysis during the signal processing step 520.

After the signals have been processed, the processor 121 may combine the signals into a current epoch array during the creation of current epoch array step 525. The current epoch array may be saved on the non-transitory computer readable medium 120 or in a database 130 operably connected to the processor 121. Once the current epoch array is created for the user 105, the processor may analyze the current epoch array to determine the psychological state 137 of the user 105 during step 530. In one embodiment, the processor 121 may compare the current epoch array to a plurality of baseline epochs 131, wherein each baseline epoch 132 within the plurality of baseline epochs 131 corresponds to a defined psychological state 137. The baseline epoch 132 within the plurality of baseline epochs 131 that most closely resembles the user's 105 current epoch array may correspond to the user's 105 psychological state 137. If the processor 121 cannot determine the psychological state 137 of a user 105, the method may return to step 510. If the processor 121 determines the psychological state 137 of the user 105, the method may proceed to step 555. In one embodiment, the method for determining a psychological state 137 of a user 105 may further comprise the step of storing a plurality of baseline epochs 131 within a database 130 operably connected to the processor 121.

During the environmental condition sensing step 535, the at least one context sensor 115 may sense an environmental condition of the user 105. The at least one context sensor 115 may detect environmental conditions of a user 105 such as geospatial data, temperature, humidity, etc. When an environmental condition is sensed by the at least one context sensor 115, the environmental condition data may be transmitted to the processor 121 during the environmental condition transmission step 540. Once the processor 121 receives the environmental condition data from the at least one context sensor 115, the processor 121 may perform instructions stored on the non-transitory computer readable medium 120 that instruct the processor 121 to determine the contextual state 138 of the user 105 during step 550. If the processor 121 cannot determine a contextual state 138 of the user 105, the method may return to step 535. If the processor 121 determines a contextual state 138 of the user 105, the method may proceed to step 555.

Once the psychological state 137 of the user 105 and the contextual state 138 of the user 105 have been determined, the processor 121 may analyze the contextual state 138 in terms of the psychological state 137 of the user 105 to determine a vector of action 136. In one embodiment, a machine learning technique, such as artificial intelligence, may analyze the psychological state 137 and the contextual state 138 to determine a vector of action 136. If the processor

121 cannot determine a vector of action 136 based on the contextual state 138 and psychological state 137 of the user 105, the method may return to step 505. If the processor 121 determines a vector of action 136 for the user 105 based on the psychological state 137 and the contextual state 138, the method may proceed to the determination of interface actions step 560. During step 560, the processor 121 may determine interface actions 142 to assign to a user based on the vector of action 136.

Once an interface action 142 is assigned to a user 105 by the processor 121, the processor 121 may determine whether an interface action 142 should be displayed for the user 105 or automatically carried out on the user's 105 behalf during step 565. If the processor 121 determines that an interface action 142 should not be provided to a user 105 via a display, the interface action 142 may be carried out by the system 100 for the user 105 automatically, and the method may proceed to the terminate method step 575. If the processor 121 determines that an interface action 142 should be provided to the user 105 via a display, the method may proceed to the display interface action step 570. Interface actions 142 may be provided to a user 105 in step 570. In one embodiment, interface actions 142 may be provided to a user 105 via a visual display, but the system 100 may provide interface actions 142 to a user 105 via an auditory, cutaneous, kinesthetic, olfactory, and gustatory display, or any combination thereof. Once the interface action 142 has been provided to the user 105, the method may proceed to the terminate method step 575.

The subject matter described herein may be embodied in systems, apparatuses, methods, and/or articles depending on the desired configuration. In particular, various implementations of the subject matter described herein may be realized in digital electronic circuitry, integrated circuitry, specially designed application specific integrated circuits (ASICs), computer hardware, firmware, software, and/or combinations thereof. These various implementations may include implementation in one or more computer programs that may be executable and/or interpretable on a programmable system including at least one programmable processor, which may be special or general purpose, coupled to receive data and instructions from, and to transmit data and instructions to, a storage system, at least one input device, and at least one output device.

These computer programs, which may also be referred to as programs, software, software applications, applications, components, or code, may include machine instructions for a programmable processor, and may be implemented in a high-level procedural and/or object-oriented programming language, and/or in assembly machine language. As used herein, the term "computer readable medium" refers to any computer program, product, apparatus, and/or device, such as magnetic discs, optical disks, memory, and Programmable Logic Devices (PLDs), used to provide machine instructions and/or data to a programmable processor, including a non-transitory computer readable medium that receives machine instructions as a computer-readable signal. The term "computer-readable signal" refers to any signal used to provide machine instructions and/or data to a programmable processor. To provide for interaction with a user, the subject matter described herein may be implemented on a computer having a display device, such as a cathode ray tube (CRD), liquid crystal display (LCD), light emitting display (LED) monitor for displaying information to the user and a keyboard and a pointing device, such as a mouse or a trackball, by which the user may provide input to the computer.

Other kinds of devices may be used to facilitate interaction with a user as well. For example, feedback provided to the user may be any form of sensory feedback, such as visual feedback, auditory feedback, or tactile feedback; and input from the user may be received in any form including, but not limited to, acoustic, speech, or tactile input. The subject matter described herein may be implemented in a computing system that includes a back-end component, such as a data serve, or that includes a middleware component, such as an application server, or that includes a front-end component, such as a client computer having a graphical user interface or a Web browser through which a user may interact with systems described herein, or any combination of such back-end, middleware, or front-end components. The components of the system may be interconnected by any form or medium of digital data communication, such as a communication network. Examples of communication networks may include, but are not limited to, a local area network ("LAN"), a wide area network ("WAN"), metropolitan area networks ("MAN"), and the internet.

The implementations set forth in the foregoing description do not represent all implementations consistent with the subject matter described herein, but are examples consistent with the disclosed subject matter. Although variations have been described in detail above, other modifications or additions may be possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein do not necessarily require the particular order shown, or sequential order, to achieve desirable results. It will be readily understood to those skilled in the art that various other changes in the details, materials, and arrangements of the parts and method stages which have been described and illustrated in order to explain the nature of this inventive subject matter may be made without departing from the principles and scope of the present disclosure.

What is claimed is:

1. A system for creating and automatically performing a device action, said system comprising:

at least one user sensor secured to a wearable device, wherein said at least one user sensor is configured to detect and transmit at least one user signal produced by a biological process of said user;

at least one context sensor, wherein said at least one context sensor is configured to detect an environmental condition of said user and to transmit environmental condition data;

a processor operably connected to said at least one user sensor and to said at least one context sensor; and a non-transitory computer-readable medium coupled to said processor and having instructions stored thereon, which, when executed by said processor, cause said processor to perform operations comprising:

a) receiving said at least one user signal transmitted by said at least one user sensor;

b) receiving said environmental condition data transmitted by said at least one context sensor;

c) creating a current epoch array comprising at least one feature extracted from said at least one user signal;

d) determining at least one current psychological state of said user from said current epoch array;

e) determining a plurality of current contextual states of said user from said environmental condition data;

f) analyzing said plurality of current contextual states in terms of said at least one current psychological state to identify at least one current contextual state from said plurality of current contextual states to determine at least one device action responsive to both said at least one current psychological state and said at least one current contextual state of the user; and g) automatically executing said at least one device action without requiring user confirmation or explicit manual user input;

h) storing said at least one device action, said at least one current contextual state, and said at least one current psychological state as an impact moment;

i) repeating steps c)-h); and j) continuously or at a predetermined rate analyzing impact moments to create at least one contextual-cortical driver, wherein said at least one contextual-cortical driver identifies commonalities between contextual states and physiological states of the impact moments while continuing to analyze current contextual states in terms of current psychological states.

2. The system of claim 1, wherein said at least one user sensor comprises at least one of an electroencephalogram machine, electromyogram machine, electrocardiogram machine, electrocorticography machine, electrodermal activity machine, functional near-infrared spectroscopy machine, infrared spectroscopy machine, temperature sensor, microphone, and eye tracking sensor.

3. The system of claim 1, wherein said at least one context sensor comprises at least one of a microphone, camera, gyroscope, accelerometer, magnetometer, pressure sensor, temperature sensor, gas sensor, eye tracking sensor, global positioning system, triangulation sensor, time-of-flight sensor, pedometer, respiratory sensor, and service application.

4. The system of claim 1, wherein the device action comprises automatically modifying the user's environment.

5. The system of claim 1, wherein said operations further comprise:

automatically executing subsequent device actions based on said contextual-cortical driver without requiring user confirmation or explicit manual user input.

\*   \*   \*   \*   \*